United States Patent
Twomey et al.

(10) Patent No.: US 8,961,515 B2
(45) Date of Patent: Feb. 24, 2015

(54) ELECTROSURGICAL INSTRUMENT

(75) Inventors: John R. Twomey, Longmont, CO (US); James D. Allen, IV, Broomfield, CO (US); Edward M. Chojin, Boulder, CO (US); Dylan R. Kingsley, Broomfield, CO (US); Jeffrey R. Unger, Longmont, CO (US)

(73) Assignee: Covidien LP, Mansfield, MA (US)

( * ) Notice: Subject to any disclaimer, the term of this patent is extended or adjusted under 35 U.S.C. 154(b) by 716 days.

(21) Appl. No.: 13/247,795

(22) Filed: Sep. 28, 2011

(65) Prior Publication Data

US 2013/0079762 A1    Mar. 28, 2013

(51) Int. Cl.
*A61B 17/00* (2006.01)
*A61B 18/14* (2006.01)
*A61B 17/29* (2006.01)

(52) U.S. Cl.
CPC ..... *A61B 18/1445* (2013.01); *A61B 2018/1455* (2013.01); *A61B 2017/2932* (2013.01); *A61B 2017/2933* (2013.01)
USPC .......................................................... 606/52

(58) Field of Classification Search
None
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| 4,881,550 A | 11/1989 | Kothe |
| 5,037,430 A | 8/1991 | Hasson |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H1745 H | 8/1998 | Paraschac |

(Continued)

FOREIGN PATENT DOCUMENTS

| | | |
|---|---|---|
| CN | 201299462 | 9/2009 |
| DE | 2415263 | 10/1975 |

(Continued)

OTHER PUBLICATIONS

U.S. Appl. No. 08/926,869, filed Sep. 10, 1997, James G. Chandler.

(Continued)

*Primary Examiner* — Brian T Gedeon

(57) ABSTRACT

An electrosurgical forceps is provided with a shaft that extends from a housing of the electrosurgical forceps. An end effector assembly operably coupled to a distal end of the shaft includes a pair of first and second jaw members each having jaw housing and an electrosurgical seal plate. One or both of the first and second jaw members is movable from an open configuration, to a clamping configuration. The moveable jaw member includes an elongated channel defined in its respective jaw housing and extends along a length thereof. A drive assembly operably couples to the moveable jaw member via a drive rod that is engageable with the elongated channel to move the movable jaw member from the open configuration to the clamping configuration and to provide a closure force between the first and second jaw members when the jaw members are in the clamping configuration.

4 Claims, 4 Drawing Sheets

(56) References Cited

U.S. PATENT DOCUMENTS

| | | |
|---|---|---|
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| 8,585,736 B2 * | 11/2013 | Horner et al. ............... 606/207 |
| 2006/0069388 A1 | 3/2006 | Truckai et al. |
| 2011/0186614 A1 | 8/2011 | Kasvikis |

FOREIGN PATENT DOCUMENTS

| | | |
|---|---|---|
| DE | 2514501 | 10/1976 |
| DE | 2627679 | 1/1977 |
| DE | 3214810 | 11/1983 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 19946527 | 12/2001 |
| DE | 10045375 | 10/2002 |
| DE | 10 2004 026179 | 12/2005 |
| DE | 20 2007 009165 | 10/2007 |
| DE | 20 2007 009317 | 10/2007 |
| DE | 20 2007 016233 | 3/2008 |
| DE | 19738457 | 1/2009 |
| DE | 10 2008 018406 | 7/2009 |
| EP | 1159926 | 12/2001 |
| JP | 61-501068 | 9/1984 |
| JP | 6-502328 | 3/1992 |
| JP | 5-5106 | 1/1993 |
| JP | 5-40112 | 2/1993 |
| JP | 6-030945 | 2/1994 |
| JP | 6-121797 | 5/1994 |
| JP | 6-285078 | 10/1994 |
| JP | 6-343644 | 12/1994 |
| JP | 6-511401 | 12/1994 |
| JP | 7-265328 | 10/1995 |
| JP | 8-56955 | 3/1996 |
| JP | 8-317936 | 3/1996 |
| JP | 8-289895 | 5/1996 |
| JP | 8-252263 | 10/1996 |
| JP | 8-317934 | 12/1996 |
| JP | 9-10223 | 1/1997 |
| JP | 9-122138 | 5/1997 |
| JP | 10-24051 | 1/1998 |
| JP | 11-070124 | 5/1998 |
| JP | 10-155798 | 6/1998 |
| JP | 2000-102545 | 9/1998 |
| JP | 11-47150 | 2/1999 |
| JP | 11-169381 | 6/1999 |
| JP | 11-192238 | 7/1999 |
| JP | 11-244298 | 9/1999 |
| JP | 2000-342599 | 12/2000 |
| JP | 2000-350732 | 12/2000 |
| JP | 2001-8944 | 1/2001 |
| JP | 2001-29356 | 2/2001 |
| JP | 2001-128990 | 5/2001 |
| JP | 2001-190564 | 7/2001 |
| JP | 2001-3400 | 11/2001 |
| JP | 2002-528166 | 3/2002 |
| JP | 2003-245285 | 9/2003 |
| JP | 2004-517668 | 6/2004 |
| JP | 2004-528869 | 9/2004 |
| JP | 2011-125195 | 6/2011 |
| SU | 401367 | 11/1974 |
| WO | WO 00/36986 | 6/2000 |
| WO | WO 00/59392 | 10/2000 |
| WO | WO 01/15614 | 3/2001 |
| WO | WO 01/54604 | 8/2001 |
| WO | WO 03/047436 | 6/2003 |
| WO | WO 2005/110264 | 11/2005 |

OTHER PUBLICATIONS

U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 12/876,668, filed Sep. 7, 2010, Sara E. Anderson.
U.S. Appl. No. 12/895,020, filed Sep. 30, 2010, Jeffrey M. Roy.
U.S. Appl. No. 12/896,100, filed Oct. 1, 2010, Ryan Artale.
U.S. Appl. No. 12/897,346, filed Oct. 4, 2010, Ryan Artale.
U.S. Appl. No. 12/906,672, filed Oct. 18, 2010, Kathy E. Rooks.
U.S. Appl. No. 12/915,809, filed Oct. 29, 2010, Thomas J. Gerhardt, Jr.
U.S. Appl. No. 12/947,352, filed Nov. 16, 2010, Jason L. Craig.
U.S. Appl. No. 12/947,420, filed Nov. 16, 2010, Jason L. Craig.
U.S. Appl. No. 12/948,081, filed Nov. 17, 2010, Boris Chernov.
U.S. Appl. No. 12/948,144, filed Nov. 17, 2010, Boris Chernov.
U.S. Appl. No. 12/950,505, filed Nov. 19, 2010, David M. Garrison.
U.S. Appl. No. 12/955,010, filed Nov. 29, 2010, Paul R. Romero.
U.S. Appl. No. 12/955,042, filed Nov. 29, 2010, Steven C. Rupp.
U.S. Appl. No. 12/981,771, filed Dec. 30, 2010, James D. Allen, IV.
U.S. Appl. No. 12/981,787, filed Dec. 30, 2010, John R. Twomey.
U.S. Appl. No. 13/006,538, filed Jan. 14, 2011, John W. Twomey.
U.S. Appl. No. 13/028,810, filed Feb. 16, 2011, Robert M. Sharp.
U.S. Appl. No. 13/030,231, filed Feb. 18, 2011, Jeffrey M. Roy.
U.S. Appl. No. 13/050,182, filed Mar. 17, 2011, Glenn A. Horner.
U.S. Appl. No. 13/072,945, filed Mar. 28, 2011, Patrick L. Dumbauld.
U.S. Appl. No. 13/080,383, filed Apr. 5, 2011, David M. Garrison.
U.S. Appl. No. 13/085,144, filed Apr. 12, 2011, Keir Hart.

(56) References Cited

OTHER PUBLICATIONS

U.S. Appl. No. 13/089,779, filed Apr. 19, 2011, Yevgeniy Fedotov.
U.S. Appl. No. 13/091,331, filed Apr. 21, 2011, Jeffrey R. Townsend.
U.S. Appl. No. 13/102,573, filed May 6, 2011, John R. Twomey.
U.S. Appl. No. 13/102,604, filed May 6, 2011, Paul E. Ourada.
U.S. Appl. No. 13/108,093, filed May 16, 2011, Boris Chernov.
U.S. Appl. No. 13/108,129, filed May 16, 2011, Boris Chernov.
U.S. Appl. No. 13/108,152, filed May 16, 2011, Boris Chernov.
U.S. Appl. No. 13/108,177, filed May 16, 2011, Boris Chernov.
U.S. Appl. No. 13/108,196, filed May 16, 2011, Boris Chernov.
U.S. Appl. No. 13/108,441, filed May 16, 2011, Boris Chernov.
U.S. Appl. No. 13/108,468, filed May 16, 2011, Boris Chernov.
U.S. Appl. No. 13/111,642, filed May 19, 2011, John R. Twomey.
U.S. Appl. No. 13/111,678, filed May 19, 2011, Nikolay Kharin.
U.S. Appl. No. 13/113,231, filed May 23, 2011, David M. Garrison.
U.S. Appl. No. 13/157,047, filed Jun. 9, 2011, John R. Twomey.
U.S. Appl. No. 13/162,814, filed Jun. 17, 2011, Barbara R. Tyrrell.
U.S. Appl. No. 13/166,477, filed Jun. 22, 2011, Daniel A. Joseph.
U.S. Appl. No. 13/166,497, filed Jun. 22, 2011, Daniel A. Joseph.
U.S. Appl. No. 13/179,919, filed Jul. 11, 2011, Russell D. Hempstead.
U.S. Appl. No. 13/179,960, filed Jul. 11, 2011, Boris Chernov.
U.S. Appl. No. 13/179,975, filed Jul. 11, 2011, Grant T. Sims.
U.S. Appl. No. 13/180,018, filed Jul. 11, 2011, Chase Collings.
U.S. Appl. No. 13/183,856, filed Jul. 15, 2011, John R. Twomey.
U.S. Appl. No. 13/185,593, filed Jul. 19, 2011, James D. Allen, IV.
U.S. Appl. No. 13/204,841, filed Aug. 8, 2011, Edward J. Chojin.
U.S. Appl. No. 13/205,999, filed Aug. 9, 2011, Jeffrey R. Unger.
U.S. Appl. No. 13/212,297, filed Aug. 18, 2011, Allan J. Evans.
U.S. Appl. No. 13/212,308, filed Aug. 18, 2011, Allan J. Evans.
U.S. Appl. No. 13/212,329, filed Aug. 18, 2011, Allan J. Evans.
U.S. Appl. No. 13/212,343, filed Aug. 18, 2011, Duane E. Kerr.
U.S. Appl. No. 13/223,521, filed Sep. 1, 2011, John R. Twomey.
U.S. Appl. No. 13/227,220, filed Sep. 7, 2011, James D. Allen, IV.
U.S. Appl. No. 13/228,742, filed Sep. 9, 2011, Duane E. Kerr.
U.S. Appl. No. 13/231,643, filed Sep. 13, 2011, Keir Hart.
U.S. Appl. No. 13/234,357, filed Sep. 16, 2011, James D. Allen, IV.
U.S. Appl. No. 13/236,168, filed Sep. 19, 2011, James D. Allen, IV.
U.S. Appl. No. 13/236,271, filed Sep. 19, 2011, Monte S. Fry.
U.S. Appl. No. 13/243,628, filed Sep. 23, 2011, William Ross Whitney.
U.S. Appl. No. 13/247,778, filed Sep. 28, 2011, John R. Twomey.
U.S. Appl. No. 13/247,795, filed Sep. 28, 2011, John R. Twomey.
U.S. Appl. No. 13/248,976, filed Sep. 29, 2011, James D. Allen, IV.
U.S. Appl. No. 13/249,013, filed Sep. 29, 2011, Jeffrey R. Unger.
U.S. Appl. No. 13/249,024, filed Sep. 29, 2011, John R. Twomey.
U.S. Appl. No. 13/251,380, filed Oct. 3, 2011, Duane E. Kerr.
U.S. Appl. No. 13/277,373, filed Oct. 20, 2011, Glenn A. Horner.
U.S. Appl. No. 13/277,926, filed Oct. 20, 2011, David M. Garrison.
U.S. Appl. No. 13/277,962, filed Oct. 20, 2011, David M. Garrison.
U.S. Appl. No. 13/293,754, filed Nov. 10, 2011, Jeffrey M. Roy.
U.S. Appl. No. 13/306,523, filed Nov. 29, 2011, David M. Garrison.
U.S. Appl. No. 13/306,553, filed Nov. 29, 2011, Duane E. Kerr.
U.S. Appl. No. 13/308,104, filed Nov. 30, 2011, John R. Twomey.
U.S. Appl. No. 13/308,147, filed Nov. 30, 2011, E. Christopher Orton.
U.S. Appl. No. 13/312,172, filed Dec. 6, 2011, Robert J. Behnke, II.
U.S. Appl. No. 13/324,863, filed Dec. 13, 2011, William H. Nau, Jr.
U.S. Appl. No. 13/337,699, filed Dec. 27, 2011, David A. Schechter.
U.S. Appl. No. 13/344,729, filed Jan. 6, 2012, James D. Allen, IV.
U.S. Appl. No. 13/355,829, filed Jan. 23, 2012, John R.Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/358,657, filed Jan. 26, 2012, Kim V. Brandt.
U.S. Appl. No. 13/360,925, filed Jan. 30, 2012, James H. Orszulak.
U.S. Appl. No. 13/369,152, filed Feb. 8, 2012, William H. Nau, Jr.
U.S. Appl. No. 13/400,290, filed Feb. 20, 2012, Eric R. Larson.
U.S. Appl. No. 13/401,964, filed Feb. 22, 2012, John R. Twomey.
U.S. Appl. No. 13/404,435, filed Feb. 24, 2012, Kim V. Brandt.
U.S. Appl. No. 13/404,476, filed Feb. 24, 2012, Kim V. Brandt.

Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectomy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.

(56) References Cited

OTHER PUBLICATIONS

Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04709033.7 dated Dec. 8, 2010.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 004429.2 dated Nov. 2, 2010.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 016911.5 extended dated Mar. 2, 2011.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report EP 10 167655.9 dated Aug. 31, 2011.
Int'l Search Report EP 10 168705.1 dated Oct. 4, 2010.

(56) References Cited

OTHER PUBLICATIONS

Int'l Search Report EP 10 169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.
Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.
Int'l Search Report EP 11 180182.5 dated Nov. 15, 2011.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28534 dated Dec. 19, 2003.
Int'l Search Report PCT/US03/28539 dated Jan. 6, 2004.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.

* cited by examiner

ELECTROSURGICAL INSTRUMENT

BACKGROUND

1. Technical Field

The present disclosure relates to an electrosurgical instrument and, more particularly, to an electrosurgical instrument including a drive assembly in operable communication with an end effector to effect movement of one or both of a pair of jaw members from a spaced-apart configuration to a closed or clamping position.

2. Description of Related Art

Electrosurgical forceps are well known in the medical arts. For example, an electrosurgical endoscopic forceps is utilized in surgical procedures, e.g., laparoscopic surgical procedures, where access to tissue is accomplished through a cannula or other suitable device positioned in an opening on a patient. The endoscopic forceps, typically, includes a housing, a handle assembly including a movable handle, a drive assembly, a shaft and an end effector assembly attached to a distal end of the shaft. The end effector includes jaw members that operably communicate with the drive assembly to manipulate tissue, e.g., grasp and seal tissue. Typically, the endoscopic forceps utilizes both mechanical clamping action and electrical energy to effect hemostasis by heating the tissue and blood vessels to coagulate, cauterize, seal, cut, desiccate, and/or fulgurate tissue.

To effect movement of the jaw members, certain types of endoscopic forceps utilize a cam slot and cam pin configuration located at a distal end of the shaft adjacent the jaw members. In particular, a drive rod of the drive assembly, typically, includes a cam pin extending from a distal end thereof. The cam pin is, typically, integrally formed with the drive rod or, in certain instances, is operably coupled thereto via one or more coupling methods, e.g., soldering, brazing, welding, etc. The cam pin is operably coupled to one or more cam slots that are disposed on the jaw members. For example, in the instance where each of the jaw members is configured to rotate or move, i.e., a bilateral jaw configuration, each of the jaw members may include a respective cam slot that is configured to operably couple to the cam pin on the drive rod. Alternatively, one of the jaw members is movable with respect to the other jaw member, e.g., a unilateral jaw configuration. In this instance, one of the jaw members includes a cam slot that is configured to couple to the cam pin on the drive rod.

As can be appreciated, forming a drive rod with a cam pin and, subsequently, positioning the cam pin within the one or more cam slots on the jaw members may increase manufacturing costs of the electrosurgical endoscopic instrument and/or increase production. Moreover, and in the instance where the cam pin is not integrally formed with the drive rod, e.g., soldering is used to join the cam pin to the drive rod, there exists the likelihood of the cam pin uncoupling from the drive rod during use thereof, which, in turn, may result in the electrosurgical endoscopic device not functioning as intended. That is, one or both of the movable jaw members may not move from an open configuration to a clamping configuration or vice versa.

In addition to the foregoing, it is sometimes desirable to provide a specific closure force at the jaw members when the jaw members are in the clamping configuration. To achieve this desired closure force, one or more devices, e.g., a resilient member such as, for example, a spring, may be operably coupled to the jaw members, drive rod, handle assembly, or other device associated with the electrosurgical endoscopic instrument. As can be appreciated, having to add the resilient member to the electrosurgical endoscopic instrument may further increase manufacturing costs of the electrosurgical endoscopic instrument and/or increase production time of the electrosurgical endoscopic instrument.

SUMMARY

An aspect of the present disclosure provides an electrosurgical forceps. The electrosurgical forceps is provided with a shaft that extends from a housing of the electrosurgical forceps. A longitudinal axis is defined through the shaft. An end effector assembly operably coupled to a distal end of the shaft includes a pair of first and second jaw members. Each of the first and second jaw member having a jaw housing and an electrosurgical seal plate. One or both of the first and second jaw members is movable from an open configuration, to a clamping configuration. The moveable jaw member includes an elongated channel defined in its respective jaw housing and extends along a length thereof. A drive assembly operably couples to the moveable jaw member via a drive rod that is engageable with the elongated channel to move the movable jaw member from the open configuration to the clamping configuration and to provide a closure force between the first and second jaw members when the jaw members are in the clamping configuration.

According to an aspect of the present disclosure, the drive rod and the elongated channel are in horizontal registration with one another to facilitate moving the at least one movable jaw member from the open configuration to the clamping configuration. The drive rod may include a generally rounded distal end to reduce a drag force thereagainst during distal translation of the drive rod within the elongated channel. The drive rod may be positioned above a pivot pin that couples the first and second jaw members.

According to a further aspect of the present disclosure, each of the first and second jaw members may be moveable from the open configuration to the clamping configuration. In this instance, the first and second jaw members may include an elongated channel defined in its respective jaw housing and extending along a length thereof. Moreover, the drive rod may include a bifurcated distal end defined by a top portion and a bottom portion that engage the respective elongated channels of the first and second jaw members during distal translation thereof to close the first and second jaw members about tissue. In certain instances, a cutting element may be operably disposed between the top portion and the bottom portion of the bifurcated distal end of the drive rod. In this instance, the cutting element may include a generally arcuate configuration having a cutting edge extending from the top portion of the bifurcated distal end to the bottom portion of the bifurcated distal end to sever tissue subsequent to the first and second jaw members clamping tissue. In certain instances, the elongated channels of the first and second jaw members may include an open distal end that allows the top and bottom portions of the bifurcated distal end to extend therepast during a cutting motion.

Another aspect of the present disclosure provides an electrosurgical forceps. The electrosurgical forceps is provided with a shaft that extends from a housing of the electrosurgical forceps. A longitudinal axis is defined through the shaft. An end effector assembly operably coupled to a distal end of the shaft includes a pair of first and second jaw members. One or both of the first and second jaw members is movable from an open configuration, to a clamping configuration. The moveable jaw member including a camming member having a generally arcuate configuration at a proximal end thereof. A drive assembly is in operative communication with the moveable jaw member via a drive rod engageable with the camming member of the movable jaw member to move the movable jaw member from the open configuration to the clamping configuration and to provide a closure force between the first and second jaw members when the jaw members are in the clamping configuration.

According to an aspect of the present disclosure, the one or more drive rods may include a cutting blade that is operably disposed at a distal end thereof. In this particular instance, the distal end of the drive rod may include a tapered configuration having a shoulder portion configured to contact the generally arcuate proximal end of the at least one moveable jaw member to move the at least one moveable jaw member from the open configuration to the clamping configuration.

A further aspect of the present disclosure provides method for electrosurgically treating and, subsequently, severing tissue. Tissue is positioned between a pair of first and second jaw members of an electrosurgical device that includes a drive assembly with a drive rod having a bifurcated distal end in operative communication with the first and second jaw members. The drive assembly including the bifurcated distal end is configured to move the first and second jaw members from an open configuration for positioning tissue therebetween, to a clamping configuration for grasping tissue therebetween. The bifurcated distal end is defined by a top and bottom portion that have a cutting element operably disposed therebetween. The bifurcated distal end is moved to position the bifurcated distal end between the first and second jaw members to clamp the tissue. Electrosurgical energy is transmitted to seal plates operably disposed on the first and second jaw members to electrosurgically treat the tissue. And, the bifurcated distal end is moved to position the top and bottom portions thereof at least partially past corresponding open distal ends of the first and second jaw members to sever tissue.

According to an aspect of the present disclosure, the type of electrosurgical transmitted may include but is not limited to electrical energy, thermal energy, ultrasonic energy and mechanical energy.

BRIEF DESCRIPTION OF THE DRAWING

Various embodiments of the present disclosure are described hereinbelow with references to the drawings, wherein.

DETAILED DESCRIPTION

Figure 1:
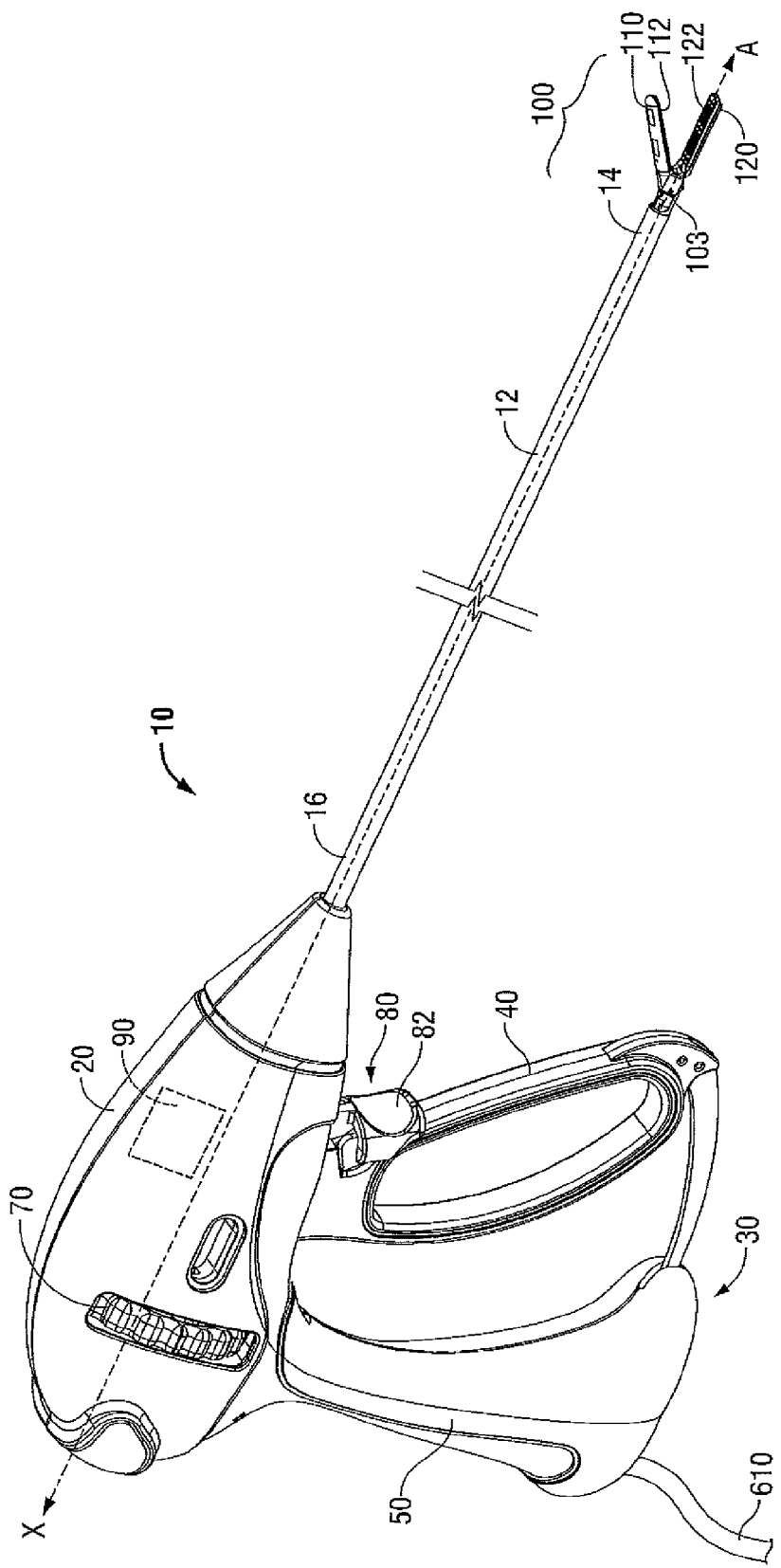
FIG. 1 is a perspective view of an endoscopic electrosurgical forceps according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Embodiments of the present disclosure are described in detail with reference to the drawing figures wherein like reference numerals identify similar or identical elements. As used herein, the term "distal" refers to the portion that is being described which is further from a user, while the term "proximal" refers to the portion that is being described which is closer to a user.

Turning now to FIG. 1, an electrosurgical endoscopic forceps 10 (forceps 10) is provided having a longitudinal axis "A-A" defined therethrough, a housing 20, a handle assembly 30, a rotating assembly 70, a trigger assembly 80 and an end effector assembly 100. Forceps 10 further includes a shaft 12 having a distal end 14 configured to mechanically engage end effector assembly 100 and a proximal end 16 that mechanically engages housing 20. Forceps 10 also includes electrosurgical cable 610 that connects forceps 10 to a generator (not shown) or other suitable power source, although forceps 10 may alternatively be configured as a battery powered instrument. Cable 610 includes a wire (or wires) (not shown) extending therethrough that has sufficient length to extend through shaft 12 in order to provide electrosurgical energy to at least one of the jaw members 110 and 120 of end effector assembly 100. As defined herein, electrosurgical energy can include, but is not limited to electrical energy, thermal energy, ultrasonic energy, mechanical energy or any suitable combination thereof. As can be appreciated, the specific configuration of the forceps, i.e., the specific type of electrosurgical energy utilized to treat tissue, may depend on, for example, the type of surgical procedure being performed, the type of tissue that is to be treated, etc. For illustrative purposes, the forceps 10 utilizes electrical energy to electro surgically treat tissue.

Rotating assembly 70 is rotatable in either direction about longitudinal axis "A-A" to rotate end effector 100 about longitudinal axis "A-A." Housing 20 houses the internal working components of forceps 10, such as a drive assembly 90 (shown in phantom in FIG. 1), working components of the handle assembly, electrical raceways associated with the cable 610, and other working components therein.

With continued reference to FIG. 1, handle assembly 30 includes fixed handle 50 and a moveable handle 40. Fixed handle 50 is integrally associated with housing 20 and handle 40 is moveable relative to fixed handle 50. Moveable handle 40 of handle assembly 30 is ultimately connected to the drive assembly 90 such that, together, handle 40 and drive assembly 90 mechanically cooperate to impart movement of jaw members 110 and 120 between a spaced-apart position and a clamping position to grasp tissue disposed between sealing surfaces 112 and 122 of jaw members 110, 120, respectively. As shown in FIG. 1, moveable handle 40 is initially spaced-apart from fixed handle 50 and, correspondingly, jaw members 110, 120 are in the spaced-apart position. Moveable handle 40 is depressible from this initial position to a depressed position corresponding to the approximated position of jaw members 110, 120.

End effector assembly 100 is designed as a unilateral assembly, i.e., where jaw member 120 is fixed relative to shaft 12 and jaw member 110 is moveable about pivot 103 relative to shaft 12 and fixed jaw member 120. However, end effector assembly 100 may alternatively be configured as a bilateral assembly, i.e., where both jaw member 110 and jaw member 120 are moveable about a pivot 103 relative to one another and to shaft 12, see FIG. 3A for example. In some embodiments, a knife assembly (see FIGS. 3A-5, for example) is disposed within shaft 12 and a knife channel (not shown) is defined within one or both jaw members 110, 120 to permit reciprocation of a knife blade (see FIGS. 3A-5, for example) therethrough, e.g., via activation of trigger 82 of trigger assembly 80. A more detailed description of a suitable knife assembly including knife blade is discussed below with reference to FIGS. 3-5.

Drive assembly 90 includes a drive a drive rod 91 (FIGS. 2A and 2B) that extends through the shaft 12 for operative communication with the end effector to effect relative movement of the jaw members 110 and 120. In the embodiment illustrated in FIGS. 1-2B, drive rod 91 is positioned above a pivot pin 103 that couples the jaw members 110 and 120. Drive rod 91 is engageable with an elongated channel 114 defined in jaw member 110 to move jaw member 110 from the open configuration (FIGS. 1 and 2A) to the clamping configuration (FIG. 2B) relative to the jaw member 120. Drive rod 91 is configured to provide a closure force at the jaw members 110 and 120 when the jaw members 110 and 120 are in the clamping configuration, described in greater detail below.

Figure 2A:
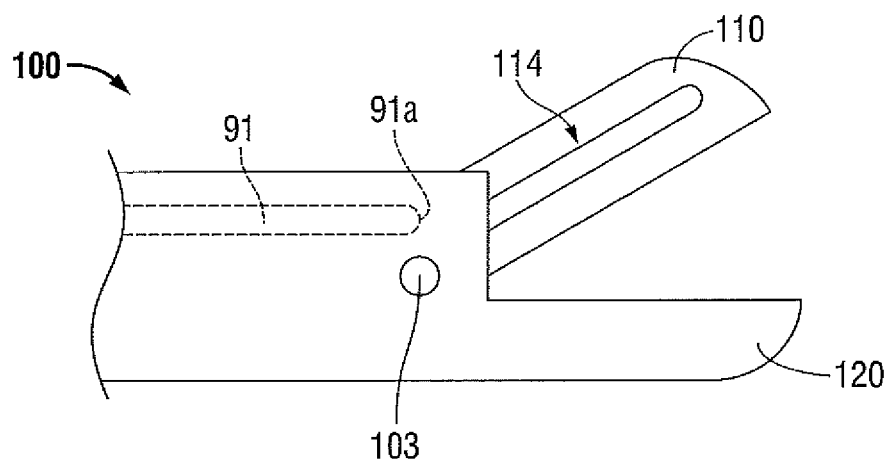
FIGS. 2A and 2B are schematic, side views of a pair of jaw members operably associated with the forceps of FIG. 1 with the jaw members in an open and clamping configuration, respectively.
Figure 2B:
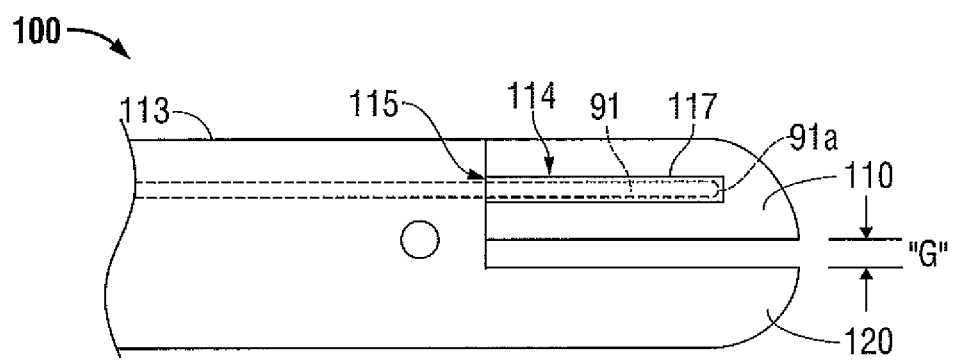

In the embodiment illustrated in FIGS. 1-2B, drive rod 91 includes a generally rounded distal end 91a to reduce a drag force thereagainst during distal translation of the drive rod 91 within the elongated channel 114 (see FIGS. 2A and 2B).

Drive rod 91 and the elongated channel 114 are in horizontal registration with one another to facilitate movement of jaw member 110 from the open configuration to the clamping configuration (FIGS. 2A and 2B) relative to the jaw member 120.

With reference again to FIG. 1, end effector assembly 100 is shown attached at a distal end 14 of shaft 12 and includes opposing jaw members 110 and 120. Each jaw member 110 and 120 includes an electrically conductive tissue sealing surface 112, 122, respectively. Moveable jaw member (in this embodiment jaw member 110), includes the elongated channel 114. In particular, channel 114 includes an opening 115 at a proximal end 113 of the jaw member 110 and extends along a length thereof (see FIGS. 2A and 2B). The length (or depth) and width of the channel 114 is proportioned to accommodate movement of the drive rod 91 therein to achieve a closure force at the jaw members 110 and 120 when the jaw members 110 and 120 are in the clamping configuration. Moreover, and in certain instances, the length (or depth) and width of the channel 114 is proportioned to accommodate movement of the drive rod 91 therein to achieve a gap distance "g" between the jaw members 110 and 120 when the jaw members 110 and 120 are in the clamping configuration. That is, the channel 114 is configured such that contact between the drive rod 91 and interior walls, i.e., an upper interior wall 117, that define the channel 114 limits movement of jaw member 110 past a predetermined position that provides a gap distance "g" between the jaw members 110 and 120 when the jaw members 110 and 120 are in the clamping position, as best seen in FIG. 2B.

In use, jaw members 110 and 120 are, initially, in an open configuration to position tissue therebetween (FIGS. 1 and 2A). Proximal movement of the movable handle 40 drives the drive rod 91 to engage the channel 114 and move within the confines of the channel 114, which, in turn, moves jaw member 110 from the open configuration (FIGS. 1 and 2A) to the clamping position (FIG. 2B). Having the drive rod 91 engage the channel 114 overcomes the aforementioned drawbacks that are typically associated with conventional forceps. In one embodiment, the unique configuration of the drive rod 91 and channel 114 provides an effective method of moving the jaw member 110 from the open configuration to the clamping configuration and an effective method of obtaining a desired closure force (e.g., between about 3 kg/cm$^3$ to about 16 kg/cm$^3$, or in certain embodiments below 3 kg/cm$^3$ and above 16 kg/cm$^3$) at the jaw members 110 and 120 without the need of a cam pin and spring as is typically required with conventional forceps. Additionally, the unique configuration of the drive rod 91 and channel 114 may provide an effective method for maintaining a specific gap distance "g" between the jaw members 110 and 120 when the jaw members 110 and 120 are in the clamping position.

Figure 3A:
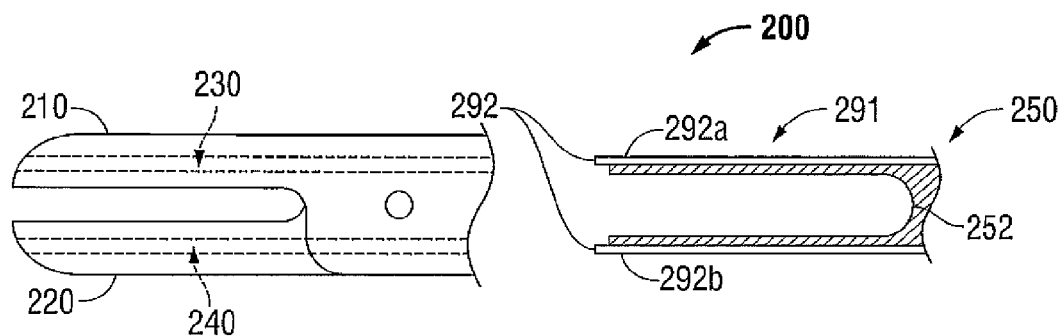
FIGS. 3A-3C are schematic, plan views of a pair of jaw members according to another embodiment of the present disclosure.

With reference to FIG. 3A, an end effector 200 including jaw members 210 and 220 according to an alternate embodiment of the present disclosure that may be utilized with the forceps 10 is illustrated. Only those operative features that are unique to the functionality of the forceps 10 that utilize the end effector 200 are described herein.

Unlike the jaw members 110 and 120 that implement a unilateral jaw configuration, each of jaw members 210 and 220 is configured to move from the open configuration to the clamping configuration, i.e., a bilateral jaw configuration. In the embodiment illustrated in FIGS. 3A-4, a pair of elongated channels 230 and 240 are operably disposed on respective jaw members 210 and 220. In one embodiment, such as, for example, the embodiment illustrated in FIGS. 3A-3C, the channels 230 and 240 include an open distal end that facilitates cutting tissue clamped between the jaw members 210 and 220. Channels 230 and 240 are configured to receive a respective top and bottom portion 292a and 292b of a bifurcated distal end 292 of a drive rod 291.

Figure 4:
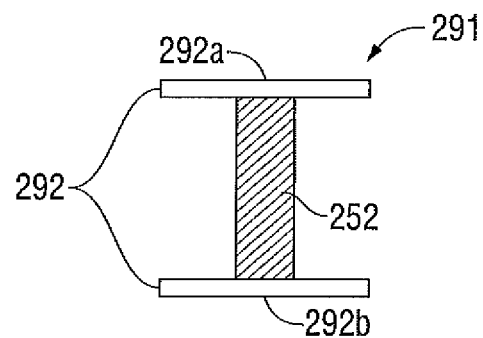
FIG. 4 is a front view of a drive member depicted in FIG. 3.

Top and bottom portions 292a and 292b are spaced-apart from one another and collectively define a generally "I" beam configuration, as best seen in FIG. 4. The top and bottom portions 292a and 292b, respectively, are each configured to translate within respective channels 230 and 240 as a result of the drive rod 291 translating distally. The top and bottom portions 292a and 292b, respectively, and the channels 230 and 240 are configured to function similar that of the drive rod 91 and channel 114. That is, in the clamping position, the top and bottom portions 292a and 292b, respectively, and the channels 230 and 240 are configured to provide the requisite closure force at the jaw members 210 and 220 when the jaw members 210 and 220 are in the clamping configuration. Moreover, the top and bottom portions 292a and 292b, respectively, and the channels 230 and 240 may be configured to provide the requisite gap distance "g" between the jaw members 210 and 220 when the jaw members 210 and 220 are in the clamping configuration.

Figure 3B:
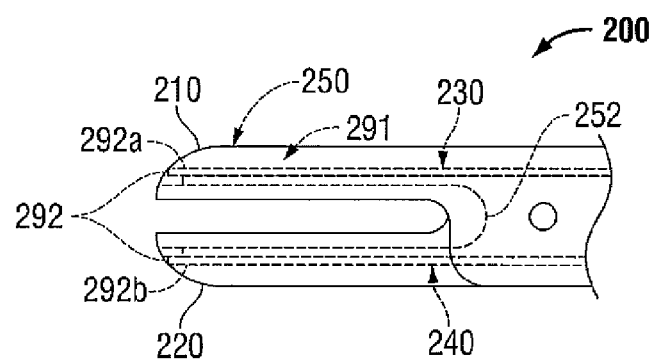
Figure 3C:
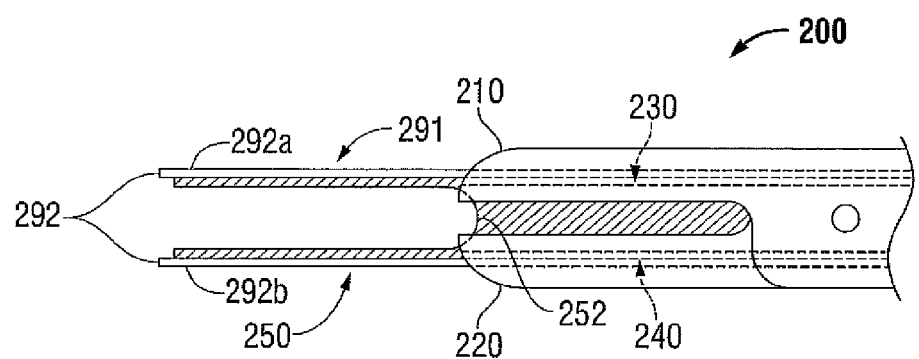

A cutting element 250 is operably disposed between the top portion 292a and the bottom portion 292b of the bifurcated distal end 292. In the embodiment illustrated in FIGS. 3A, 3B and 4, the cutting element 250 includes a generally arcuate configuration that has a cutting edge 252. The cutting edge 252 extends from the top portion 292a of the bifurcated distal end 292 to the bottom portion 292b of the bifurcated distal end 292. The cutting element 250 is configured to sever tissue subsequent to the jaw members 110 and 120 clamping down on tissue. In particular, the cutting edge 252 of the cutting element 250 is "set-back" so as not to sever tissue until the top and bottom portions 292a and 92b, respectively, have traveled a predetermined distance within the corresponding channels 230 and 240. That is, a predetermined distance that corresponds to the jaw members 210 and 220 being in the clamping position with the requisite closure force present at the jaw members 210 and 220 and a requisite gap distance "g" between the jaw members 210 and 220 (FIG. 3B). Once tissue is clamped and/or sealed, the drive rod 291 may be moved further distally through a cutting motion such that the cutting edge 252 severs tissue disposed between jaw members 210 and 220. In this instance, the top and bottom portions 292a and 292b extend beyond the distal end of the jaw members 210 and 220 to cut tissue, as best seen in FIG. 3C.

In certain embodiments, it may prove advantageous to provide one or more members, e.g., nub, protrusion, detent, indent, etc., in the channels 230 and 240 to indicate to or otherwise inform an end user, e.g., a surgeon, that the top and bottom portions 292a and 292b, respectively, have translated a predetermined distance therein. That is, a predetermined distance that corresponds to the jaw members 210 and 220 being in the clamping position with the requisite closure force present at the jaw members 210 and 220 and a requisite gap distance "g" between the jaw members 210 and 220.

In use, jaw members 210 and 220 are, initially, in an open configuration to position tissue therebetween. Proximal movement of the movable handle 40 drives the drive rod 291, which, in turn, moves the top and bottom portions 292a and 292b within the confines of the respective cam slots 230 and 240, which, in turn, moves jaw members 210 and 220 from the open configuration to the clamping position (FIG. 3A). The unique configuration of the bifurcated distal end 291 including the top and bottom portions 292a and 292b, respectively, is configured to selectively engage the corresponding cam slots 230 and 240 overcomes the aforementioned drawbacks that are typically associated with conventional forceps. Once tissue is clamped and/or sealed, the drive rod 291 may be moved further distally such that the cutting edge 252 severs tissue disposed between jaw members 210 and 220. In this instance, the top and bottom portions 292a and 292b extend beyond the distal end of the jaw members 210 and 220 to cut tissue (FIG. 3C).

Figure 5:
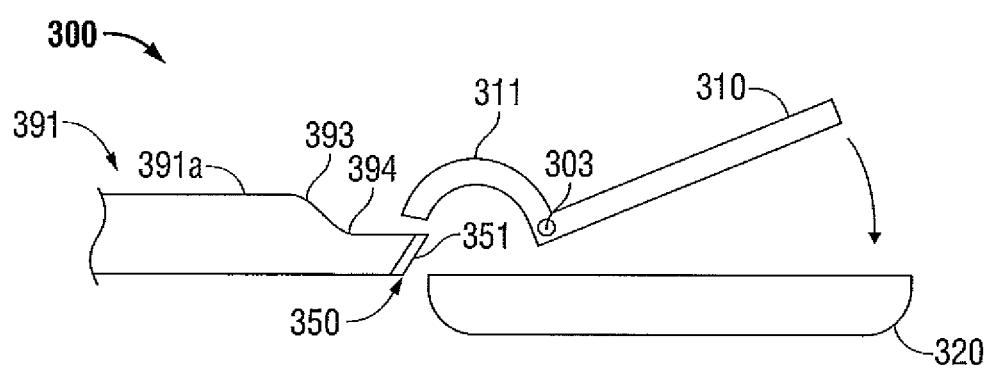
FIG. 5 is schematic, plan view of a pair of jaw members according to another embodiment of the present disclosure.

With reference to FIG. 5, an end effector 300 including jaw members 310 and 320 according to another embodiment of the present disclosure that may be utilized with the forceps 10 is illustrated. Only those operative features that are unique to the functionality of the forceps 10 that utilize the end effector 300 are described herein.

In the embodiment illustrated in FIG. 5, jaw members 310 and 320 include a jaw configuration similar to that of jaw members 110 and 120, i.e., a unitary jaw configuration, wherein jaw member 310 is movable and jaw member 320 is stationary. To move jaw member 310 from the open configuration to the clamping configuration, jaw member 310 includes a camming member 311 of suitable configuration that is configured to contact a distal portion 391a of a drive rod 391. In particular, the camming member 311 is operably disposed at a proximal end of the jaw member 310 and includes a generally arcuate configuration that upon contact with the distal portion 391 causes the jaw member 310 to pivot about pivot pin 303 to move jaw member 310 to the clamping configuration. Moreover, and in the clamping configuration, camming member 311 may be configured to provide the requisite closure force at and gap distance "g" between the jaw members 310 and 320 (similar to FIG. 2B).

Distal portion 391a includes a tapered configuration having a shoulder portion 393 configured to contact the camming member 311 of jaw member 310 to move jaw member 310 from the open configuration to the clamping configuration. Distal portion 391 includes a generally elongated neck portion 394 of suitable configuration that extends a predetermined distance from the shoulder portion 393. In the embodiment illustrated in FIG. 5, the neck portion 394 is configured to operably couple to or otherwise support a cutting blade thereon.

Cutting blade 350 is of suitable configuration to sever or otherwise separate tissue. Cutting blade 350 includes a cutting edge 351 having a generally slanted or oblique configuration to facilitate severing tissue. In the embodiment illustrated in FIG. 5, the cutting edge 351 includes a generally flat configuration, although, in certain instances, the cutting edge 351 may be serrated. The elongated portion 391 and cutting blade 350 including cutting edge 351 are configured such that jaw members 310 and 320 will be in the clamping configuration with the requisite closure force at and gap distance "g" between the jaw members 310 and 320 prior to the cutting blade 350 advancing to severe tissue.

In use, jaw members 310 and 320 are, initially, in an open configuration to position tissue therebetween (FIG. 5). Proximal movement of the movable handle 40 drives the drive rod 391. As drive rod 391 is moved distally, the shoulder 393 contacts the camming member 311 of the jaw member 310, which, in turn, moves jaw member 310 from the open configuration to the clamping configuration. The unique configuration of the drive rod 391 and the camming member 311 of the jaw member 310 provides an effective method of moving the jaw member 310 from the open configuration to the clamping configuration and an effective method of obtaining a desired closure force (e.g., between about 3 kg/cm$^3$ to about 16 kg/cm$^3$, or in certain embodiments below 3 kg/cm$^3$ and above 16 kg/cm$^3$) at the jaw members 310 and 320 without the need of a cam pin and spring as is typically required with conventional forceps. Additionally, the unique configuration of the drive rod 391 and the camming member 311 of the jaw member 310 provides an effective method for maintaining a specific gap distance "g" between the jaw members 310 and 320 when the jaw members 310 and 320 are in the clamping position. Once tissue is clamped and sealed, the drive rod 391 may be moved further distally such that the cutting edge 351 severs tissue disposed between jaw members 310 and 320.

From the foregoing and with reference to the various figure drawings, those skilled in the art will appreciate that certain modifications can also be made to the present disclosure without departing from the scope of the same. For example, in certain instances, one or more springs (not shown) may be operably associated with either of the aforementioned end effectors 100, 200 and 300. The one or more springs may be configured to provide a specific closure force at the jaw members, 110, 210, 310 and 120, 220, 320.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical forceps, comprising:
   a housing having a shaft extending therefrom;
   an end effector assembly operably coupled to a distal end of the shaft and including a pair of first and second jaw members each having a jaw housing and an electrosurgical sealing plate, each of the first and second jaw members movable from an open configuration for positioning tissue therebetween, to a clamping configuration for grasping tissue therebetween, each of the first and second jaw members including an elongated channel defined in its respective jaw housing and extending along a length thereof; and
   a drive assembly operably coupled to the at least one moveable jaw member via a drive rod, the drive rod including a bifurcated distal end defined by a top portion and a bottom portion that engage the respective elongated channels of the first and second jaw members during distal translation thereof to close the first and second jaw members about tissue and to provide a closure force between the first and second jaw members when the first and second jaw members are in the clamping configuration.

2. An electrosurgical forceps according to claim 1, wherein the top and bottom portions of the drive rod and the respective elongated channels are in horizontal registration with one another to facilitate moving the first and second jaw members from the open configuration to the clamping configuration.

3. An electrosurgical forceps according to claim 1, wherein a cutting element is operably disposed between the top portion and the bottom portion of the bifurcated distal end of the drive rod, the cutting element including a generally arcuate configuration having a cutting edge extending from the top portion of the bifurcated distal end to the bottom portion of the bifurcated distal end to sever tissue subsequent to the first and second jaw members clamping tissue.

4. An electrosurgical forceps according to claim 1, wherein the elongated channels of the first and second jaw members include an open distal end that allows the top and bottom portions of the bifurcated distal end to extend therepast during a cutting motion.

* * * * *